US00PP09244P

United States Patent [19]

Fruehwirth

[11] Patent Number: Plant 9,244

[45] Date of Patent: Aug. 15, 1995

[54] POINSETTIA PLANT '718'

[75] Inventor: Franz Fruehwirth, Encinitas, Calif.

[73] Assignee: Paul Ecke Ranch, Inc., Encinitas, Calif.

[21] Appl. No.: 253,961

[22] Filed: Jun. 2, 1994

[51] Int. Cl.[6] ..... A01H 5/00
[52] U.S. Cl. ..... Plt./86.4
[58] Field of Search ..... Plt. 86.4

[56] References Cited

U.S. PATENT DOCUMENTS

P.P. 5,492 6/1985 Gutbier ..... Plt./86.4
P.P. 7,874 5/1992 Fruehwirth ..... Plt./86.4
4,724,276 2/1988 Ecke, Jr. ..... 47/58

*Primary Examiner*—Howard J. Locker
*Attorney, Agent, or Firm*—Arnold, White & Durkee

[57] ABSTRACT

Poinsettia '718' is a new cultivar, distinguished by rich red flower bracts, dark green foliage, self-branching characteristics, and 10-week flowering response time. The new plant produces a very desirable branched flowering pot plant for the late season holiday market. Poinsettia '718' is resistant to epinasty after being confined to shipping containers. The post-production foliage and bract retention is excellent even under low light intensities in the consumer's home.

1 Drawing Sheet

BACKGROUND OF THE NEW PLANT

This new poinsettia cultivar, '718' originated as an induced self-branching sport of a seedling known as 'L-41' in inventor's greenhouse in Encinitas, Calif. 'L-41' is a proprietary plant and there are no specimens in the public domain. '718' was selected because of its bright, rich red flower bracts, dark green foliage, self-branching characteristics, and natural flowering after Dec. 1 in Encinitas, Calif. under natural daylight conditions; traits which distinguish it from other poinsettia cultivars, and seem to make it a desirable plant for commercial greenhouse production. After seslection, '718' was vegetatively reproduced from stem cuttings for test purposes in Encinitas, Calif. By subjecting clones of this plant to successive generations of vegetative propagation, it was demonstrated that the distinctive characteristics of '718' held true from generation to generation.

DESCRIPTION OF THE PHOTOGRAPHS

Poinsettia '718' is illlustrated in the accompanying color photographs. The upper photo is a side view of 3 single stem plants per pot in full flower. Evidence of self-branching can be seen in the flowering axillary branches beneath the upper canopy of bracts. The lower photo is a top view of the same plants showing flower and bract formation.

DESCRIPTION OF THE PLANT

Cultivar '718' is "self-branching" in that, during development, axillary branches elongate without pinching (removal of the apical bud) and if under short day conditions, the axillary branches will develop flowers. The parent cultivar, 'L-41' is not self-branching in that no axillary branches develop as long as the apical bud is not removed (pinched).

When cultivars '718' and 'L-41' were pinched (removal of the apical bud) axillary shoots elongated and developed flowers at each of the nodes on cultivar '718'. There were eight to ten uniformly developed branches. In contrast, only three to four axillary branches elongated and developed flowers after removal of the apical bud on cultivar 'L-41', even though eight to ten nodes remained on the stem after pinching.

The following chart shows a comparison of the new cultivar '718' with other known cultivars '140' U.S. Plant Pat. No. (PP7874) and 'Angelika' U.S. Plant Pat. No. (PP5492). Cultivar 'L-41' was a proprietary plant and there are no specimens in the public domain. 'L-41' was a seedling obtained from cross-pollination. It had no "self-branching" traits.

| | '718 | '140 | Angelika |
|---|---|---|---|
| Flower Response Time | 10 Weeks | 8 Weeks | 9 Weeks |
| Bract Color | RHS 45A–45B (Bright Red) | RHS 46A (Dull, Dark Red with Bluish Tones) | — |
| Leaf Color (Undersurface) | RHS 147A–147B (Dark Green) | RHS 191A (Grey-Green) | — |
| Height (December '93) | 33 cm | 37 cm | — |
| Leaf Color | RHS 147A (Dark Green | — | RHS 147A (Medium Green) |
| Leaf Retention (Indoors) | Up to 10 Weeks | — | 3 Weeks |

DESCRIPTION OF THE PLANT

The following is a detailed description of this new poinsettia as observed in Encinitas, Calif., U.S.A. during December 1993. Observations were recorded from flowering plants, grown as 3 single stem plants per pot. The pot was 14 cm in diameter and 11 cm in height. Color designations are compared to the 1986 edition of R.H.S. Colour Chart, first published in 1966 by The Royal Horticultural Society, London, England.

THE PLANT

Origin: Sport of a seedling. The sport was induced by application of the procedures set forth in U.S. Pat. No. 4,724,276 to the seedling plant. Root stock used was Angelika (U.S. Plant Pat. No. 5,492).

Classification:

*Botanic.*—*Euphorbia pulcherrima* Willd.

*Common name.*—Poinsettia.

*Cultivar name.*—'718'.

Form: Shrub.

Height: Short to medium.

Growth habit: As a single stemmed plant, upright and vigorous with self-branching side shoots. The application of a chemical growth retardant may not be needed to restrict height for commercial pot plant production. I observed 3 unpinched plants in a pot with an overall height of 37 cm and an overall width of 46 cm. The bract diameter of individual flowers was 26 cm.

Branching: Axillary branches will develop and terminate in a flower without pinching. However, it is usually desirable to pinch '718' before flower induction and remove all terminal dominance. Then, all axillary branches will develop uniformly and at a faster rate.

Growth rate: Rooting of stem cutting occurs in 12–18 days under intermittent mist. The plant will flower in about ten weeks under continuous long night conditions and night temperatures of about 16–18 degrees C.

Foliage: The foliage is clean and uniformly dark green from bottom to top of the plant. The leaves are of medium size, leaf blades typically being 14–16 cm long and 10–11 cm wide with leaf petioles 4–6 cm long.

*Leaf shape.*—Typical leaves are generally ovate with obtuse bases and acuminate tips. Leaf margins are lobed with 1 or 2 indentations on each side of the leaf blade.

*Color.*—Upper side — Dark green, darker than R.H.S. 147A. Under side — Green, R.H.S. 147A–B.

*Retention.*—The foliage lasts extremely well even under low light intensities in the consumer's home.

Bracts: Generally there are 21–24 rich red bracts of various sizes subtending the cyathia. The primary bracts have blades typically 15 cm long and 11–12 cm wide with petioles about 3 cm long.

*Shape.*—Primary bracts are ovate with acute bases and acuminate tips. Primary bract margins are lobed with 1 or 2 indentations on either side of the bract. Secondary bracts are mostly elliptic of various size and have entire margins.

*Color.*—Upper side — Rich, bright red, between R.H.S. 45A–B. Small bracts near center, darker than R.H.S. 45A. Under side — Red, near R.H.S. 45B.

Flowers: Generally, 21–24 cyathia (flowers) are present when the plant is in full bloom. Each cyathium is about 6 mm long and 5 mm wide, green in color, and fringed with red at the distal end. A yellow nectar cup with reddish lips protrudes from the side of each cyathium. The flower pedicel is also green and about 5 mm in length. The stamens protruding from the cyathia are dark red. The anthers are bifurcate; the pollen is yellow and copious. The stigmas are dark red and trifurcate.

*Flowering response.*—Ten weeks after start of flower initiation.

*Cyathium.*—Cyathium retention is better than average, lasting three weeks beyond fully mature flowers.

*Nectar exudate.*—Abundant.

*Seeds.*—Self-incompatible.

*Fertility.*—Not observed.

Post production: Poinsettia '718' is resistant to epinasty after being confined to shipping containers and retains its leaves and flower bracts for several weeks in the consumer's home environment.

What is claimed is:

1. A new and distinct Poinsettia cultivar, substantially as herein shown and described, distinguished by its large rich red flower bracts, dark green foliage, and self-branching characteristics.

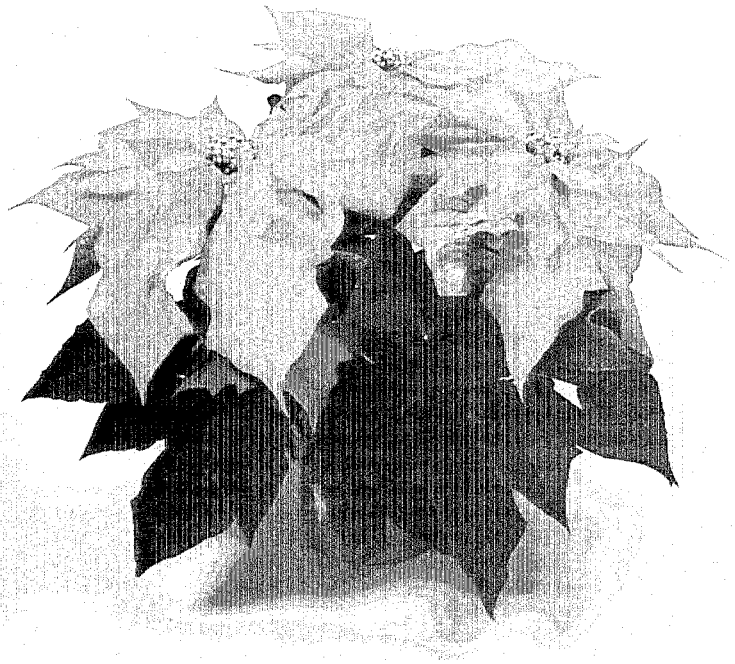
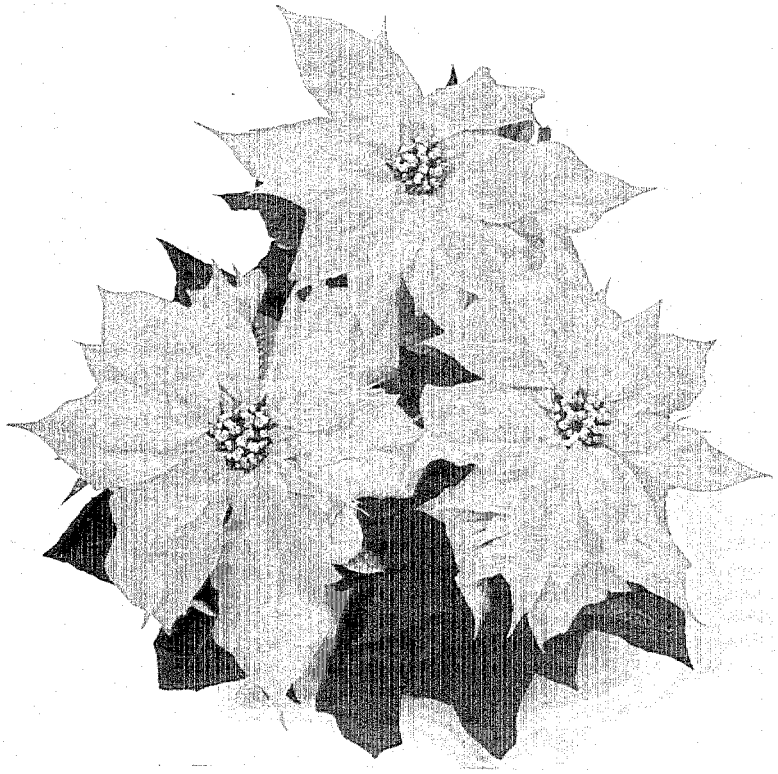

* * * * *